US006211236B1

(12) United States Patent
Müller et al.

(10) Patent No.: US 6,211,236 B1
(45) Date of Patent: Apr. 3, 2001

(54) FUNGICIDE MIXTURES

(75) Inventors: Ruth Müller, Friedelsheim; Herbert Bayer; Hubert Sauter, both of Mannheim; Eberhard Ammermann, Heppenheim; Gisela Lorenz, Hambach; Siegfried Strathmann, Limburgerhof; Klaus Schelberger, Gönnheim; Reinhold Saur, Böhl-Iggelheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/171,619

(22) PCT Filed: Apr. 22, 1997

(86) PCT No.: PCT/EP97/02020

§ 371 Date: Oct. 22, 1998

§ 102(e) Date: Oct. 22, 1998

(87) PCT Pub. No.: WO97/40674

PCT Pub. Date: Nov. 6, 1997

(30) Foreign Application Priority Data

| Apr. 26, 1996 | (DE) | 196 16 722 |
| Apr. 26, 1996 | (DE) | 196 16 725 |
| Apr. 29, 1996 | (DE) | 196 17 073 |
| Sep. 2, 1996 | (DE) | 196 35 513 |
| Sep. 2, 1996 | (DE) | 196 35 512 |
| Sep. 2, 1996 | (DE) | 196 35 507 |

(51) Int. Cl.[7] ............ A01N 37/12; A01N 37/44; A01N 37/18; A01N 43/64; A01N 55/00

(52) U.S. Cl. ............ 514/539; 514/63; 514/255.05; 514/269; 514/383; 514/399; 514/508; 514/538; 514/618; 514/619

(58) Field of Search .................. 514/508, 538, 514/618, 619, 539, 269, 383, 255.05, 399, 63

(56) References Cited

U.S. PATENT DOCUMENTS

| 5,145,856 | 9/1992 | Clough et al. | 514/274 |
| 5,264,440 | 11/1993 | Clough et al. | 514/269 |
| 5,395,837 | 3/1995 | Clough et al. | 514/269 |
| 5,468,747 | 11/1995 | Clough et al. | 514/239.5 |
| 5,504,110 | * 4/1996 | Wingert et al. | 514/539 |
| 5,981,581 | * 11/1999 | Bayer et al. | 514/222 |
| 6,066,756 | * 5/2000 | Bayer et al. | 588/440 |

FOREIGN PATENT DOCUMENTS

| 9322921 | * 11/1993 | (WO) . |
| 9521153 | * 8/1995 | (WO) . |
| 9521154 | * 8/1995 | (WO) . |

OTHER PUBLICATIONS

Pesticide Science, vol. 44, No. 1, May 1995, pp. 77–79.

* cited by examiner

*Primary Examiner*—Allen J. Robinson
(74) *Attorney, Agent, or Firm*—Keil & Weinkauf

(57) ABSTRACT

A fungicidal mixture comprising a) an oxime ether of the formula I

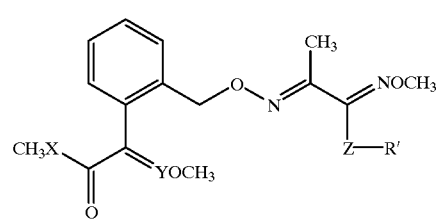

(I)

where the substituents have the following meanings:

X is oxygen or amino (NH);

Y is CH or N;

Z is oxygen, sulfur, amino (NH) or $C_1$–$C_4$-alkylamino (N-alkyl);

R' is alkyl, haloalkyl, alkenyl, haloalkenyl, alkynyl, haloalkynyl, cycloalkylmethyl, or, if desired, substituted benzyl;

a) an oxime ether of the formula I

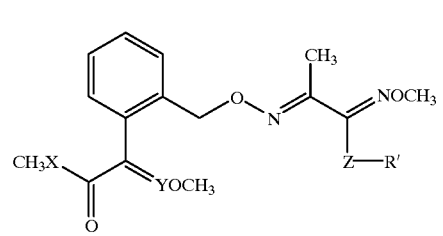

(I)

where the substituents have the following meanings:

X is oxygen or amino (NH);

Y is CH or N;

Z is oxygen, sulfur, amino (NH) or $C_1$–$C_4$-alkylamino (N—$C_1$–$C_4$-alkyl);

R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$-$C_4$-haloalkoxy and $C_1$-$C_4$-alkylthio;

and at least one compound from groups b)–c):

b.1) the oxime ether carboxylate of the formula IIa,

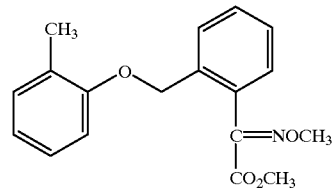
(IIa)

b.2) the oxime ether carboxamide of the formula IIb,

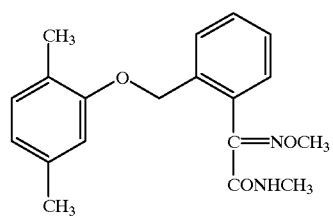
(IIb)

b.3) the methoxyacrylate of the formula IIc,

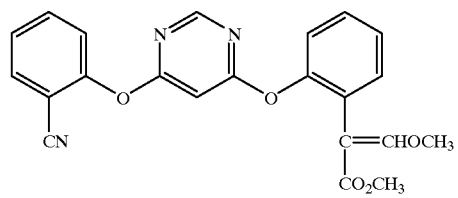
(IIc)

c) one or more azole derivatives in a synergistically active amount.

18 Claims, No Drawings

FUNGICIDE MIXTURES

This application is a 371 of PCT/EPA7/02020, filed Apr. 22, 1997.

The present invention relates to fungicidal mixtures which comprise a) an oxime ether of the formula I

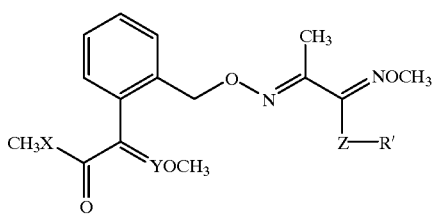

(I)

where the substituents have the following meanings:

X is oxygen or amino (NH);

Y is CH or N;

Z is oxygen, sulfur, amino (NH) or $C_1$–$C_4$-alkylamino (N—$C_1$–$C_4$-alkyl);

R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

and at least one compound from groups b)–c):

b.1) the oxime ether carboxylate of the formula IIa,

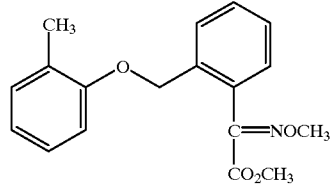

(IIa)

b.2) the oxime ether carboxamide of the formula IIb

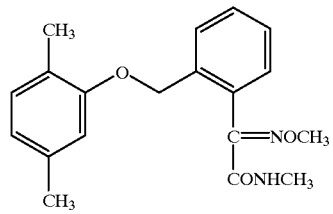

(IIb)

b.3) the methoxyacrylate of the formula IIc,

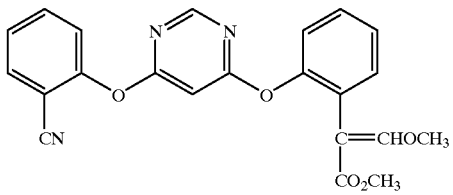

(IIc)

and/or c) an azole derivative III selected from the group of the compounds III.1 to III.17

1-[(2RS,4RS;2RS,4SR)-4-bromo-2-(2,4-dichlorophenyl)-tetrahydrofuryl]-1H-1,2,4-triazole (III.1)

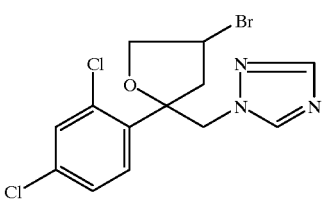

2-(4-chlorophenyl)-3-cyclopropyl-1-(1H-1,2,4-triazol-1-yl)butan-2-ol (III.2)

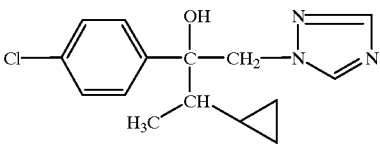

(+)-4-chloro-4-[4-methyl-2-(1H-1,2,4-triazol-1-ylmethyl)-1,3-dioxolan-2-yl]phenyl 4-chlorophenyl ether (III.3)

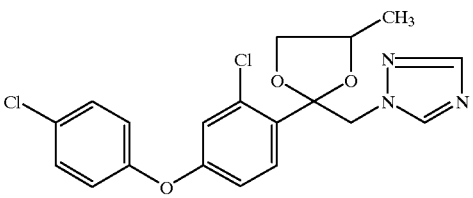

(E)-(R,S)-1-(2,4-dichlorophenyl)-4,4-dimethyl-2-(1H-1,2,4-triazol-1-yl)pent-1-en-3-ol (III.4)

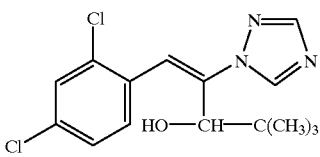

(Z)-2-(1H-1,2,4-triazol-1-ylmethyl)-2-(4-fluorophenyl)-
3-(2-chlorophenyl)oxirane (III.5)

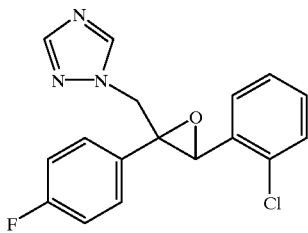

4-(4-chlorophenyl)-2-phenyl-2-(1H-1,2,4-triazolyl-
methyl)butyronitrile (III.6)

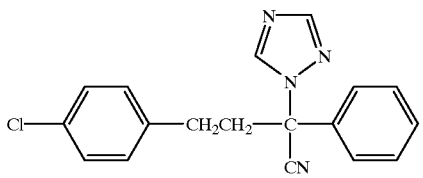

3-(2,4-dichlorophenyl)-6-fluoro-2-(1H-1,2,4-triazol-1-yl)
quinazolin-4(3H)-one (III.7)

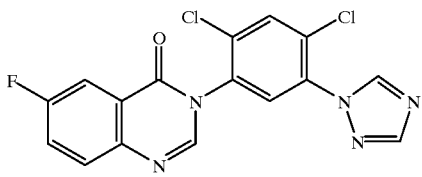

bis(4-fluorophenyl) (methyl) (1H-1,2,4-triazol-1-
ylmethyl)silane (III.8)

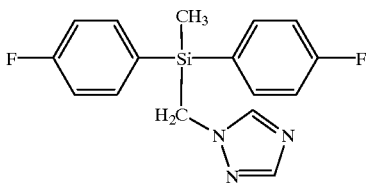

(R,S)-2-(2,4-dichlorophenyl)-1-(1H-1,2,4-triazol-1-yl)
hexan-2-ol (III.9)

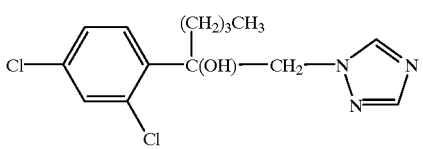

(1RS,5RS;1RS,5SR)-5-(4-chlorobenzyl)-2,2-dimethyl-1-
(1H-1,2,4-triazol-1-ylmethyl)cyclopentanol (III.10)

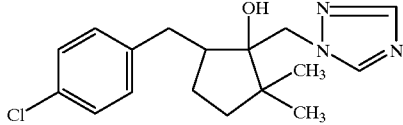

N-propyl-N-[2-(2,4,6-trichlorophenoxy)ethyl]imidazole-
1-carboxamide (III.11)

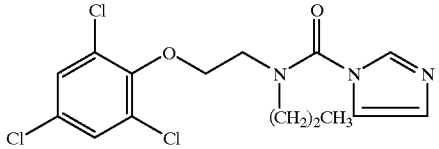

(+)-1-[2-(2,4-dichlorophenyl)-4-propyl-1,3-dioxolan-2-
ylmethyl]-1H-1,2,4-triazole (III.12)

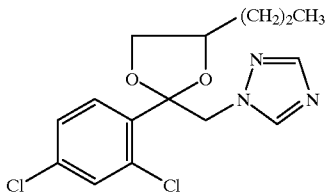

(R,S)-1-(4-chlorophenyl)-4,4-dimethyl-3-(1H-1,2,4-
triazol-1-ylmethyl)pentan-3-ol (III.13)

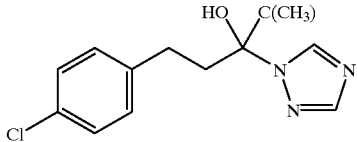

(+)-2-(2,4-dichlorophenyl)-3-(1H-1,2,4-triazolyl)-propyl
1,1,2,2-tetrafluoroethyl ether (III.14)

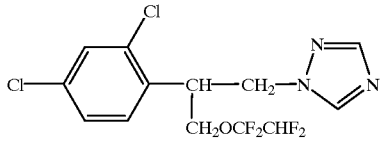

(E)-1-[1-[[4-chloro-2-(trifluoromethyl)phenyl]imino]-2-
propoxyethyl]-1H-imidazole (III.15)

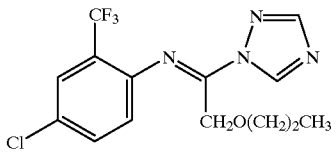

(RS)-2,4'-difluoro-α-(1H-1,2,4-triazol-1-ylmethyl)-
benzhydryl alcohol (III.16)

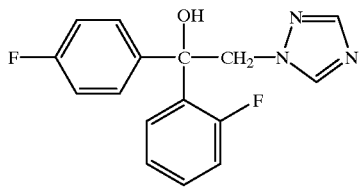

2-p-chlorophenyl-2-(1H-1,2,4-triazol-1-ylmethyl)-
hexanenitrile (III.17)

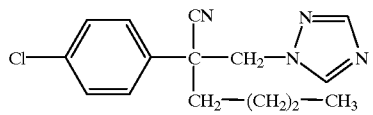

in a synergistically active amount.

Moreover, the invention relates to methods of controlling harmful fungi with mixtures of the compounds I, II and III and to the use the compounds I, II and III for the preparation of such mixtures.

The compounds I are described in the literature as fungicides and insecticides (DE Appl. No. 19 528 651.0, WO-A 95/21,153 and WO-A 95/21,154).

The compounds IIa (EP-A 253 213), IIb (EP-A 477 631) and the compound IIc (EP-A 382,375), their preparation and their activity against harmful fungi have also been disclosed.

The azole derivatives III, their preparation and their activity against harmful fungi are known to the expert from the literature:

III.1: common name: bromuconazole, Proc. Br. Crop Prot. Conf. Pests Dis., 5–6, 439 (1990);

III.2: common name: cyproconazole, U.S. Pat. No. 4,664, 696;

III.3: common name: difenoconazole, GB-A 2,098,607;

III.4: common name: diniconazole, CAS RN [83657-24-3];

III.5: common name: (proposed): epoxiconazole, EP-A 196 038;

III.6: common name: fenbuconazole (proposed), EP-A 251 775;

III.7: common name: fluquinconazole, Proc. Br. Crop Prot. Conf. Pests Dis., 5-3, 411 (1992);

III.8: common name: flusilazole, Proc. Br. Crop Prot. Conf. Pests Dis., 1, 413 (1984);

III.9: common name: hexaconazole, CAS RN [79983-71-4];

III.10: common name: metconazole, Proc. Br. Crop Prot. Conf. Pests Dis., 5-4, 419 (1992);

III.11: common name: prochloraz, U.S. Pat. No. 3,991, 071;

III.12: common name: propiconazole, GB-A 1,522,657;

III.13: common name: tebuconazole, U.S. Pat. No. 4,723, 984;

III.14: common name: tetraconazole, Proc. Br. Crop Prot. Conf. Pests Dis., 1, 49 (1988);

III.15: common name: triflumizole, JP-A 79/119,462;

III.16: common name: flutriafol, CAS RN [76674-21-0];

III.17: common name: myclobutanil, CAS RN [88671-89-0].

It was an object of the present invention to provide mixtures which have an improved activity against harmful fungi combined with a reduced total amount of active ingredients applied (synergistic mixtures) with a view to reducing the rates of application and to improving the spectrum of action of the known compounds.

Accordingly, we have found that this object is achieved by the mixtures defined at the outset. Moreover, we have found that better control of the harmful fungi is possible by applying the compounds I and II or III simultaneously together or separately or by applying the compounds I and II or III in succession than when the individual compounds are used.

In particular, the general formula I represents oxime ethers in which X is oxygen and Y is CH or X is amino and Y is N.

Moreover, preferred compounds I are those where Z is oxygen.

Equally, preferred compounds I are those where R' is alkyl or benzyl.

Especially preferred with a view to their use in the synergistic mixtures according to the invention are the compounds I compiled in the tables which follow:

(IA)

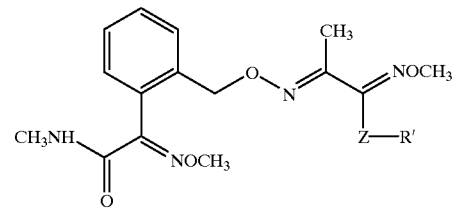

(IB)

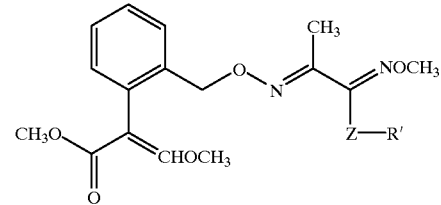

TABLE B

| No. | ZR' |
| --- | --- |
| I.1 | O—CH$_2$CH$_2$CH$_3$ |
| I.2 | O—CH(CH$_3$)$_2$ |
| I.3 | O—CH$_2$CH$_2$CH$_2$CH$_3$ |
| I.4 | O—CH(CH$_3$)CH$_2$CH$_3$ |
| I.5 | O—CH$_2$CH(CH$_3$)$_2$ |
| I.6 | O—C(CH$_3$)$_3$ |
| I.7 | S—C(CH$_3$)$_3$ |
| I.8 | O—CH(CH$_3$)CH$_2$CH$_2$CH$_3$ |
| I.9 | O—CH$_2$C(CH$_3$)$_3$ |
| I.10 | O—C(Cl)=CCl$_2$ |
| I.11 | O—CH$_2$CH=CH—Cl (trans) |
| I.12 | O—CH$_2$—C(CH$_3$)=CH$_2$ |
| I.13 | O—CH$_2$—(cyclopropyl) |
| I.14 | O—CH$_2$—C$_6$H$_5$ |
| I.15 | O—CH$_2$—[4-F—C$_6$H$_4$] |
| I.16 | O—CH$_2$—CH$_3$ |
| I.17 | O—CH(CH$_2$CH$_3$)$_2$ |

In relation to the C=Y— or C=CH— or C=N double bonds, the compounds of the formulae I and II can be in the E or the Z configuration (in relation to the carboxylic acid function). Accordingly, they can be used in the mixture according to the invention in each case either in the form of the pure E or Z isomers or else in the form of an E/Z isomer mixture. The E/Z isomer mixture or the Z isomer are preferably used, the Z isomer being especially preferred.

The C=N double bonds of the oxime ether groups in the side chain of the compounds I can be in each case in the form of pure E or Z isomers or in the form of E/Z isomer mixtures. The compounds I can be used in the mixtures according to the invention as isomer mixtures or else as pure isomers. With a view to their use, compounds I which are particularly preferred are those where the terminal oxime ether group of the side chain is in the cis configuration ($OCH_3$ relative to ZR').

Because of their basic character, the compounds I, II and III are capable of forming adducts or salts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphoric acid radicals), it being possible for the alkyl or aryl radicals to have attached, to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can in this case be in the various valences which they can assume.

When preparing the mixtures, it is preferred to employ the pure active ingredients I, II and III, with which further active ingredients against harmful fungi or other pests such as insects, arachnids or nematodes, or else herbicidal or growth-regulating active ingredients or fertilizers can be admixed, if so desired.

The present invention relates to binary mixtures of compounds I with a compound II or III; however, ternary mixtures, which comprise 3 components, may also be employed.

A preferred example of three-component mixtures are those which comprise, as component III, preferably the compounds III.1, III.4, III.5 and III.10, especially preferably the compound III.5 (epoxiconazole).

The mixtures of the compounds I and II or III, or the simultaneous joint or separate use of the compounds I, II and III, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore also be employed as foliar- and soil-acting fungicides.

They are especially important for controlling a large number of fungi in a variety of crop plants such as cotton, vegetable species (eg. cucumbers, beans and cucurbits), barley, grass, oats, coffee, maize, fruit species, rice, rye, soybeans, grapevine, wheat, ornamentals, sugar cane, and a variety of seeds.

They are particularly suitable for controlling the following phytopathogenic fungi: *Erysiphe graminis* (powdery mildew) on cereals, *Erysiphe cichoracearum* and *Sphaerotheca fuliginea* on curcubits, *Podosphaera leucotricha* on apples, Puccinia species on cereals, Rhizoctonia species on cotton, rice and lawn, Ustilago species on cereals and sugar cane, *Venturia inaequalis* (scab) on apples, Helminthosporium species on cereals, *Septoria nodorum* on wheat, *Botrytis cinerea* (gray mold) on strawberries, vegetables, ornamentals and grapevines, *Cercospora arachidicola* on peanuts, *Pseudocercosporella herpotrichoides* on wheat and barley, *Pyricularia oryzae* on rice, *Phytophthora infestans* on potatoes and tomatoes, Pseudoperonospora species on cucurbits and hops, *Plasmopara viticola* on grapevines, Alternaria species on vegetables and fruit, and Fusarium and Verticillium species.

Furthermore, they can be used in the protection of materials (eg. in the protection of wood), for example against *Paecilomyces variotii*.

The compounds I, II and III can be applied simultaneously together or separately or in succession, the sequence, in the case of separate application, generally not having any effect on the result of the control measures.

The compounds I and II are normally used in a weight ratio of from 10:1 to 0.1:1, preferably 5:1 to 0.2:1, in particular 3:1 to 0.3:1.

The compounds I and III are normally used in a weight ratio of from 10:1 to 0.1:1, preferably 5:1 to 0.5:1, in particular 3:1 to 0.2:1 (III:I).

In the case of the compounds I, the rates of application of the mixtures according to the invention are from 0.005 to 0.5 kg/ha, preferably 0.005 to 0.5 kg/ha, in particular 0.01 to 0.3 kg/ha depending on the nature of the desired effect.

Correspondingly, the rates of application of the compounds II are generally from 0.01 to 1 kg/ha, preferably 0.05 to 0.5 kg/ha, in particular 0.1 to 0.5 kg/ha.

In general, the rates of application of the compounds III are from 0.01 to 1 kg/ha, preferably 0.05 to 1 kg/ha, in particular 0.05 to 0.5 kg/ha.

For seed treatment, the application rates of the mixture are generally from 0.001 to 100 g/kg of seed, preferably 0.01 to 50 g/kg, in particular 0.01 to 10 g/kg.

If phytopathogenic harmful fungi are to be controlled, the separate or joint application of the compounds I and II or III or of the mixtures of the compounds I, II and III is effected by spraying or dusting the seeds, the plants or the soils before or after sowing of the plants, or before or after plant emergence.

The fungicidal synergistic mixtures according to the invention, or the compounds I, II and III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl polyglycol ethers or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or jointly grinding the compounds I and II or III or the mixture of the compounds I and II or III with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I, II or III, or of the mixture of the compounds I and II or III. The active ingredients are employed in a purity of from 90% to 100%, preferably 95% to 100% (according to NMR or HPLC spectrum).

The compounds I and II or III, or the mixtures, or the corresponding formulations, are applied by treating the harmful fungi or the plants, seeds, soils, areas, materials or spaces to be kept free from them with a fungicidally active amount of the mixture, or of the compounds I, II and III in the case of separate application. Application can be effected before or after infection by the harmful fungi.

The fungicidal activity of the compounds and of the mixtures is demonstrated by the following experiments:

The active ingredients, separately or together, are formulated as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

Evaluation is carried out by determining the infected leaf areas in percent. These percentages are converted into efficacies. The expected efficacies of the mixtures of the active ingredients are determined using Colby's formula [R. S. Colby, Weeds 15, 20–22 (1967)] and compared with the observed efficacies.

Colby's formula:

$$E = x+y+z-x \cdot y \cdot z/100$$

E expected efficacy, expressed in % of the untreated control, when using the mixture of the active ingredients A, B and C at concentrations of a, b and c x efficacy, expressed in % of the untreated control, when using active ingredient A at a concentration of a y efficacy, expressed in % of the untreated control, when using active ingredient B at a concentration of b z efficacy, expressed in % of the untreated control, when using active ingredient C at a concentration of c The efficacy (W) was calculated as follows using Abbot's formula:

$$W = (1-\alpha) \cdot 100/\beta$$

$\alpha$ is the fungal infection level of the treated plants in % and $\beta$ is the fungal infection level of the untreated (control) plants in %

An efficacy of 0 means that the infection level of the treated plants corresponds to that of the untreated control plants; an efficacy of 100 means that the treated plants were not infected.

EXAMPLES 1–8

Efficacy Against *Puccinia recondita* on Wheat
(Leaf Rust of Wheat)

Leaves of wheat seedlings cv. "Frühgold" grown in pots were dusted with leaf rust spores (*Puccinia recondita*). The pots were then placed for 24 hours into a chamber with high atmospheric humidity (90 to 95%) at 20 to 22° C. During this time, the spores germinated, and the germ tubes penetrated the plant tissue. The next day, the infected plants were sprayed to run-off with an aqueous spray mixture which had been made with a stock solution of 10% active ingredient, 63% cyclohexanone and 27% emulsifier. After the spray coating had dried on, the test plants were grown in the greenhouse for 7 days at from 20 to 22° C. and a relative atmospheric humidity of 65 to 70%.

The extent of fungal rust development on the leaves was then determined.

The visually determined values for the percentage of diseased leaf area were transformed into efficacies as percent of the untreated control. An efficacy of 0 means that the infection level equals that of the untreated control. An efficacy of 100 means an infection level of 0%. The expected efficacies for combinations of active ingredients were calculated using Colby's formula (Colby, S. R. "Calculating synergistic and antagonistic responses of herbicide combinations", Weeds, 15, p. 20–22, 1967) and compared with the observed efficacies.

TABLE 3

| | Active ingredient or combinations | Concentration of active ingredient in the spray mixture in ppm | Efficacy in % of the untreated control |
|---|---|---|---|
| 1V | Control (untreated) | (infection level 100%) | 0 |
| 2V | A = compound No. I.2 of Table 1 | 4 | 30 |
| | | 1 | 0 |
| 3V | Compound IIa | 4 | 0 |
| | | 1 | 0 |
| 4V | Compound IIb | 4 | 0 |
| | | 1 | 0 |

TABLE 4

| Ex. | Concentration of active ingredient in the spray mixture in ppm | Observed efficacy | Calculated efficacy*) |
|---|---|---|---|
| 5 | 4A + 4IIa | 40 | 30 |
| 6 | 1A = 1IIa | 20 | 0 |
| 7 | 4A = 4IIb | 50 | 30 |
| 8 | 1A = 1IIb | 25 | 0 |

*)calculated using Colby's formula

The test results reveal that for all mixing ratios the observed efficacy exceeds the efficacy precalculated using Colby's formula.

EXAMPLES 9–20

Efficacy Against Powdery Mildew of Wheat

Leaves of wheat seedlings cv. "Frühgold" grown in pots were sprayed to run-off with an aqueous preparation of active ingredient made with a stock solution composed of 10% active ingredient, 63% cyclohexanone and 27% emulsifier and, 24 hours after the spray coating had dried on, dusted with spores of powdery mildew of wheat (*Erysiphe graminis forma specialis tritici*). The test plants were subsequently placed in a greenhouse at from 20 to 22° C. and a relative atmospheric humidity of 75 to 80%. After 7 days, the extent of powdery mildew development was determined visually in % infected leaf area of the total leaf area.

The visually determined values for the percentage of diseased leaf area were transformed into efficacies as percent of the untreated control. An efficacy of 0 means that the infection level equals that of the untreated control. An efficacy of 100 means an infection level of 0%. The expected efficacies for combinations of active ingredients were calculated using Colby's formula (Colby, S. R. "Calculating synergistic and antagonistic responses of herbicide combinations", Weeds, 15, p. 20–22, 1967) and compared with the observed efficacies.

TABLE 5

| Ex. | Active ingredient | Concentration of active ingredient in the spray mixture in ppm | Efficacy in % of the untreated control |
|---|---|---|---|
| 9V | Control (untreated) | (infection level 92%) | 0 |
| 10V | Compound No. I.2 in accordance with Table 1 = A | 0.4 | 84 |
| 11V | Compound No. I.4 in accordance with Table 1 = B | 0.8 | 84 |
|   |   | 0.4 | 73 |
| 12V | III.8 = flusilazole | 0.4 | 14 |
| 13V | III.9 = hexaconazole | 0.4 | 0 |
| 14V | III.12 = propiconazole | 0.8 | 0 |
|   |   | 0.4 | 0 |

TABLE 6

| Ex. | Concentration of active ingredient in the spray mixture in ppm | Observed efficacy | Calculated efficacy*) |
|---|---|---|---|
| 15 | 0.4 A + 0.4 III.8 | 98 | 86 |
| 16 | 0.4 A + 0.4 III.9 | 95 | 84 |
| 17 | 0.4 A + 0.4 III.12 | 99 | 84 |
| 18 | 0.4 B + III.8 | 95 | 77 |
| 19 | 0.4 B + 0.4 III.9 | 88 | 73 |
| 20 | 0.4 B + 0.4 III.12 | 94 | 84 |

*)calculated using Colby's formula

The test results reveal that for all mixing ratios the observed efficacy exceeds the efficacy precalculated using Colby's formula.

We claim:

1. A fungicidal composition comprising synergistically effective amounts of a) an oxime ether I

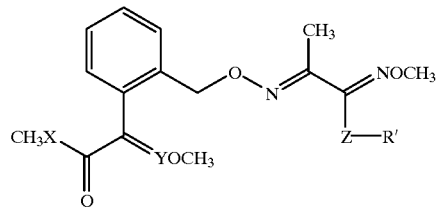

(I)

wherein the substituents have the following meaning:

X is oxygen or amino (NH);

Y is CH or N;

Z is oxygen;

R' is $C_1$–$C_6$-alkyl, $C_1$–$C_6$-haloalkyl, $C_3$–$C_6$-alkenyl or $C_2$–$C_6$-haloalkenyl, and b) a compound II selected from the group consisting of the carboxylate IIa and the carboxamide IIb:

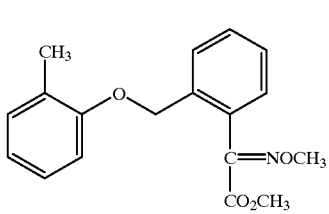

(IIa)

-continued (IIb)

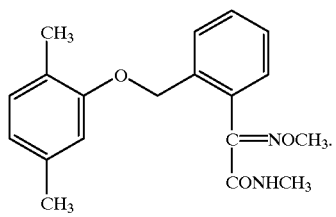

2. The composition defined in claim 1 comprising the carboxylate IIa.

3. The composition defined in claim 1 comprising the carboxamide IIb.

4. The composition defined in claim 1, comprising the oxime ether I and the compound II in a weight ratio of from 10:1 to 0.1:1.

5. The composition defined in claim 1, further comprising synergistically effective amounts of at least one azole III selected from the group consisting of the compounds 1-[(2RS,4RS;2RS4SR)-4-bromo-(2,4-dichlorophenyl) tetrahydrofuryl]-1H-1,2,4-triazole (III.1)

(III.1)

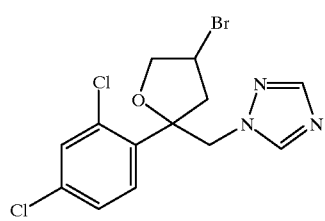

2-(4-chlorophenyl)-3-cyclopropyl-1-(1H-1,2,4-triazol-1-yl)butan-2-ol (III.2)

(III.2)

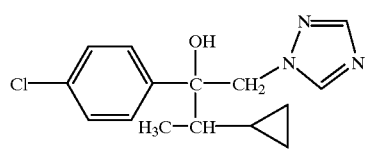

(+)-4-chloro-4-[4-methyl-2-(1H-1,2,4-triazol-1-ylmethyl)-1,3-dioxolan-2-yl]phenyl 4-chlorophenyl ether (III.3)

(III.3)

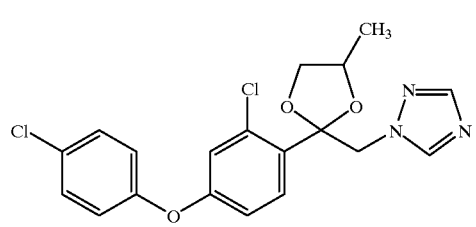

(E)-(R,S)-1-(2,4-dichlorophenyl)-4,4-dimethyl-2-(1H-1,2,4-triazol-1-yl)pent-1-en-3-ol (III.4)

(III.4)

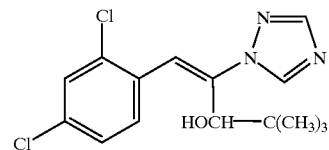

(Z)-2-(1H-1,2,4-triazol-1-ylmethyl)-2-(4-fluorophenyl)-3-(2-chlorophenyl)oxirane (III.5)

(III.5)

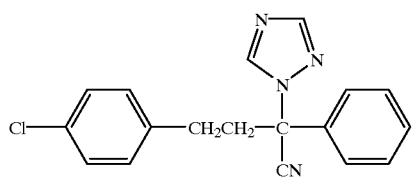

4-(4-chlorophenyl)-2-phenyl-2-(1H-1,2,4-triazolylmethyl)butyronitrile (III.6)

(III.6)

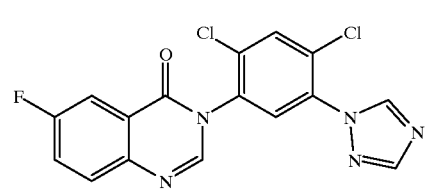

3-(2,4-dichlorophenyl)-6-fluoro-2-(1H-1,2,4-triazol-1-yl)-quinazolin-4(3H)-one (III.7)

(III.7)

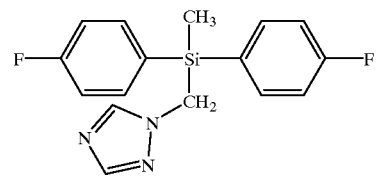

bis(-4-fluorophenyl)(methyl)(1H-1,2,4-triazol-1-ylmethyl)silane (III.8)

(III.8)

(R,S)-2-(2,4-dichlorophenyl)-1-(1H-1,2,4-triazol-1-yl)hexan-2-ol (III.9)

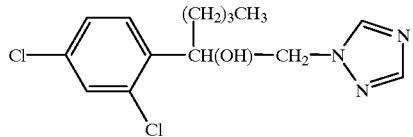
(III.9)

(1RS,5RS;1RS,5SR)-5-(4-chlorobenzyl)-2,2-dimethyl-1-(1H-1,2,4-triazol-1-ylmethyl)cyclopentanol (III.10)

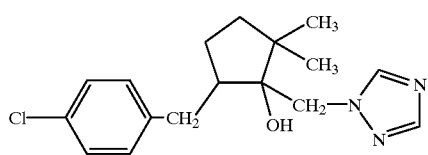
(III.10)

N-propyl-N-[2-(2,4,6-trichlorophenoxy)ethyl]imidazol-1-carboxamide (III.11)

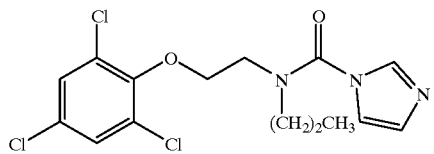
(III.11)

(+)-1-[2-(2,4-dichlorophenyl)-4-propyl-1,3-dioxolan-2-ylmethyl]-1H-1,2,4-triazole (III.12)

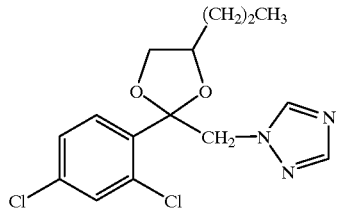
(III.12)

(R,S)-1-(4-chlorophenyl)-4,4-dimethyl-3-(1H-1,2,4-triazol-1-ylmethyl)pentan-3-ol (III.13)

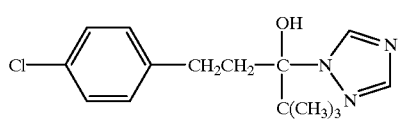
(III.13)

(+)-2-(2,4-dichlorophenyl)-3-(1H-1,2,4-triazolyl)propyl 1,1,2,2-tetrafluoroethyl ether (III.14)

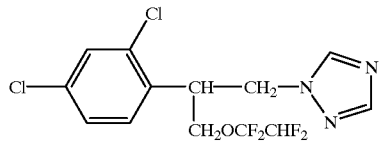
(III.14)

(E)-1-[1-[[4-chloro-2-(trifluoromethyl)phenyl]imino]-2-propoxyethyl]-1H-imidazole (III.15)

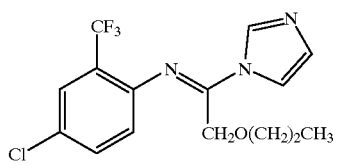
(III.15)

(R,S)-2,4'-difluoro-α-(1H-1,2,4-triazol-1-ylmethyl)benzhydryl alcohol (III.16)

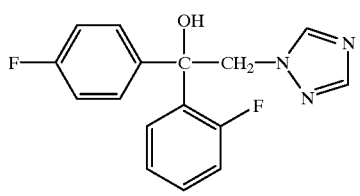
(III.16)

and
2-p-chlorophenyl-2-(1H-1,2,4-triazol-1-ylmethyl)hexanitrile (III.17)

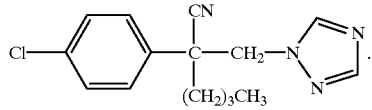
(III.17)

6. The composition defined in claim 5 wherein the azole III is the compound III.1, III.4, III.5 or III.10.

7. The composition defined in claim 5 comprising the carboxylate IIa.

8. The composition defined in claim 5 comprising the carboxamide IIb.

9. The composition defined in claim 5, comprising the oxime ether I and the compound II in a weight ratio of from 10:1 to 0.1:1.

10. The composition defined in claim 5, comprising the azole III and the oxime ether I in a weight ratio of from 10:1 to 0.1:1.

11. A method for controlling harmful fungi, which comprises treating the harmful fungi, their environment, or the plants, seeds, soils, areas, materials or spaces to be kept free from said fungi with a synergistically effective amount of an oxime ether I and a compound II as set forth in claim 1.

12. The method defined in claim 11, wherein the oxime ether I is applied in an amount of from 0.005 to 0.5 kg/ha 13. The method defined in claim 11, wherein the compound II is applied in an amount of from 0.01 to 1 kg/ha.

14. The method defined in claim 11 further comprising treating the harmful fungi, their environment, or the plants, seeds, soils, areas, materials or spaces to be kept free from said fungi with a synergistically effective amount of an azole III selected from the group consisting of the compounds 1-[(2RS,4RS;2RS,4SR)-4-bromo-(2,4-dichlorophenyl)tetrahydrofuryl]-1H-1,2,4-triazole (III.1)

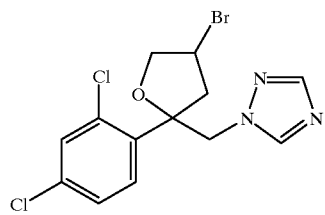

(III.1)

2-(4-chlorophenyl)-3-cyclopropyl-1-(1H-1,2,4-triazol-1-yl)butan-2-ol (III.2)

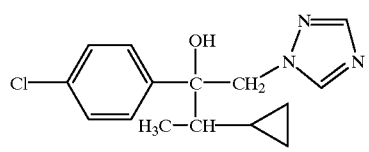

(III.2)

(+)-4-chloro-4-[4-methyl-2-(1H-1,2,4-triazol-1-ylmethyl)-1,3-dioxolan-2-yl]phenyl 4-chlorophenyl ether (III.3)

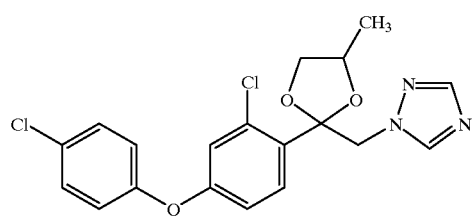

(III.3)

(E)-(R,S)-1-(2,4-dichlorophenyl)-4,4-dimethyl-2-(1H-1,2,4-triazol-1-yl)pent-1-en-3-ol (III.4)

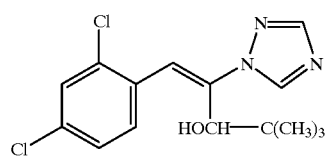

(III.4)

(Z)-2-(1H-1,2,4-triazol-1-ylmethyl)-2-(4-fluorophenyl)-3-(2-chlorophenyl)oxirane (III.5)

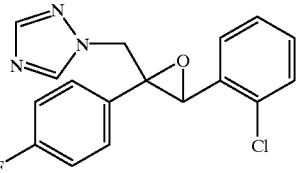

(III.5)

4-(4-chlorophenyl)-2-phenyl-2-(1H-1,2,4-triazolylmethyl)butyro-nitrile (III.6)

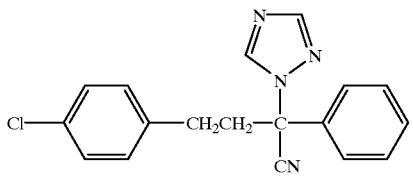

(III.6)

3-(2,4-dichlorophenyl)-6-fluoro-2-(1H-1,2,4-triazol-1-yl)-quinazolin-4(3H)-one (III.7)

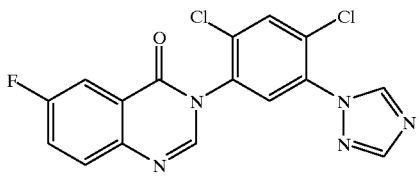

(III.7)

bis(-4-fluorophenyl)(methyl)(1H-1,2,4-triazol-1-ylmethyl)silane (111.8)

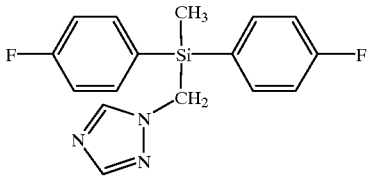

(III.8)

(R,S)-2-(2,4-dichlorophenyl)-1-(1H-1,2,4-triazol-1-yl)hexan2-ol (III.9)

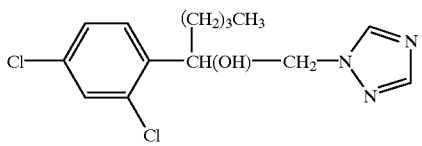

(III.9)

(1RS,5RS;1RS,5SR)-5-(4-chlorobenzyl)-2,2-dimethyl-1-
(1H-1,2,4-triazol-1-ylmethyl)cyclopentanol (III.10)

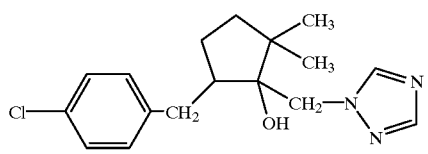
(III.10)

N-propyl-N-[2-(2,4,6-trichlorophenoxy)ethyl]imidazol-
1-carboxamide (III.11)

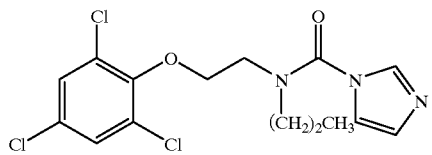
(III.11)

(+)-1-[2-(2,4-dichlorophenyl)-4-propyl-1,3-dioxolan-2-
ylmethyl]-1H-1,2,4-triazole (III.12)

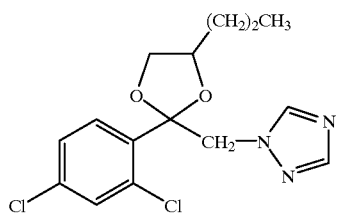
(III.12)

(R,S)-1-(4-chlorophenyl)-4,4-dimethyl-3-(1H-1,2,4-
triazol-1-ylmethyl)pentan-3-ol (III.13)

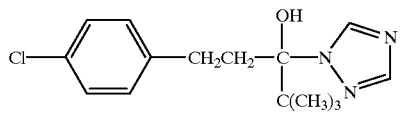
(III.13)

(+)-2-(2,4-dichlorophenyl)-3-(1H-1,2,4-triazolyl)propyl
1,1,2,2-tetrafluoroethyl ether (III.14)

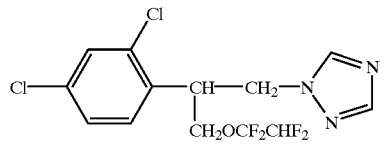
(III.14)

(E)-1-[1-[[4-chloro-2-(trifluoromethyl)phenyl]imino]-2-
propoxyethyl]-1H-imidazole (III.15)

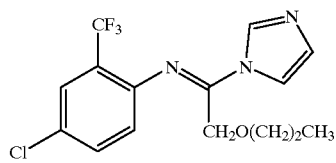
(III.15)

(R,S)-2,4'-difluoro-α-(1H-1,2,4-triazol-1-ylmethyl)
benzhydryl alcohol (III.16)

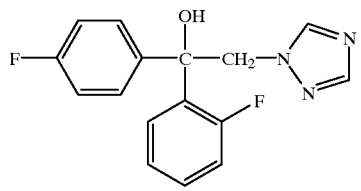
(III.16)

and
2-p-chlorophenyl-2-(1H-1,2,4-triazol-1-ylmethyl)
hexanitrile (III.17)

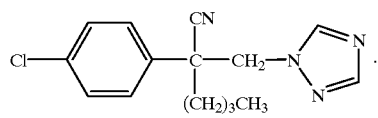
(III.17)

15. The method defined in claim 14, wherein the azole III is the compound III.1, III.4, III.5 or III.10.

16. The method defined in claim 14, wherein the oxime ether I is applied in an amount of from 0.005 to 0.5 kg/ha.

17. The method defined in claim 14, wherein the compound II is applied in an amount of from 0.01 to 1 kg/ha.

18. The method defined in claim 14, wherein the azole III is applied in an amount of from 0.01 to 1 kg/ha.

* * * * *

UNITED STATES PATENT AND TRADEMARK OFFICE
CERTIFICATE OF CORRECTION

PATENT NO. : 6,211,236 B1
DATED : April 3, 2001
INVENTOR(S) : Mueller et al.

It is certified that error appears in the above-identified patent and that said Letters Patent is hereby corrected as shown below:

<u>Column 13, claim 5,</u>
Line 24, "2RS4SR" should be -- 2RS, 4SR --.

Signed and Sealed this

Thirtieth Day of October, 2001

Attest:

*Attesting Officer*

NICHOLAS P. GODICI
*Acting Director of the United States Patent and Trademark Office*